United States Patent [19]
Maupin

[11] Patent Number: 5,834,226
[45] Date of Patent: Nov. 10, 1998

[54] ONE-STEP TEST FOR ASPARTATE AMINOTRANSFERASE

[75] Inventor: Paul Hutsell Maupin, San Diego, Calif.

[73] Assignee: Xytronyx, Inc., San Diego, Calif.

[21] Appl. No.: 648,586

[22] Filed: Jan. 31, 1991

[51] Int. Cl.⁶ .............................. C12Q 1/48; C12Q 1/52; C12Q 1/00; G01N 33/53
[52] U.S. Cl. ................... 435/15; 435/16; 435/4; 435/975; 435/7.4; 435/184; 436/63
[58] Field of Search .................... 435/15, 16, 184, 435/805, 24, 4, 7.9, 975, 7.4; 436/63; 422/55, 56

[56] References Cited

U.S. PATENT DOCUMENTS

| | | | |
|---|---|---|---|
| 3,875,014 | 4/1975 | Forgione | 435/805 |
| 4,059,407 | 11/1977 | Hochstrasser | 435/805 |
| 4,241,179 | 12/1980 | Madappally et al. | 435/16 |
| 4,801,535 | 1/1989 | Babler et al. | 435/16 |
| 4,981,787 | 1/1991 | Baram | 435/15 |
| 5,039,619 | 8/1991 | Staple et al. | 436/63 |
| 5,047,328 | 9/1991 | Chambers et al. | 435/16 |

FOREIGN PATENT DOCUMENTS

| | | |
|---|---|---|
| 117550 | 2/1984 | European Pat. Off. . |
| 3026854 | 7/1980 | Germany . |
| 3221730 | 6/1982 | Germany . |
| 188099 | 9/1985 | Japan . |
| 272998 | 11/1987 | Japan . |

OTHER PUBLICATIONS

Quiroga, et al. "A Comparison of Different Stains Used for the Detection of Aspartate Amino Transferase In Biological Samples", *Analytical Letters* 20(4):569–585 (1987).
Leinweber and Monty, 143 *Methods in Enzymology* 160 (1987), "Cysteinesulfinic Acid: Fuchsin Method".
Akasaka et al., *Anal. Lett.,* 18(B3):357–368 (1985).
Recasens et al., *Biochemistry* 19:4583–4589 (1980).
Todd–Sanford, *Clinical Diagnosis By Laboratory Methods,* Davidson et al. eds, W. B. Saunders Company, Philadelphia, PA, 14th Ed., pp. 673–748 (1969).
Yagi et al., *Anal. Biochem.,* 110:146–149 (1981).

*Primary Examiner*—Louise N. Leary
*Attorney, Agent, or Firm*—Lyon & Lyon LLP

[57] ABSTRACT

Novel assay kits and methods are described for the detection and determination of the severity of disease conditions associated with elevated levels of aspartate aminotransferase (AST). The AST levels are determined by reaction of the AST with cysteine sulfinic acid (CSA) substrate in the presence of a sulfite-reactive dye compound that is substantially nonreactive with AST or CSA, such as a triarylmethine dye. Sulfite ion formed by the reaction of AST with CSA causes a calorimetric indication of AST that can be related to a predetermined stage of disease.

20 Claims, No Drawings

ONE-STEP TEST FOR ASPARTATE AMINOTRANSFERASE

DESCRIPTION

1. Technical Field

The present invention relates to methods and assay kits for identifying diseases in mammals associated with elevated levels of the enzyme aspartate aminotransferase (AST). More particularly, the invention is applicable to the detection of human disease conditions such as heart, liver, and periodontal disease.

2. Background

Several heart and liver diseases have been correlated with abnormally high levels of serum AST. Examples of such conditions include acute myocardial infarction, pulmonary emulsion, acute pancreatitis, viral and toxic hepatitis, and acute cirrhosis. Generally speaking, AST is elevated in diseases affecting tissues rich in AST.

Extensive studies have shown that 92–98% of patients with acute myocardial infarction have elevated serum AST level. The measured levels are usually four to ten times the upper limit of normal values. The elevated AST levels develop six to twelve hours after the time of infarction and usually return to normal by the third or fourth day. Secondary rises can be correlated with other features, suggesting extension or recurrence of myocardial infarction. Also, mild elevations of serum AST levels have been reported in patients with pulmonary infarction. In patients with congestive heart failure and those with marked tachycardia, mild to moderate degrees of AST elevation may occur. These have been attributed to hepatic necrosis secondary to hepatic congestion. Patients with pericarditis also have been reported to have a fifty percent incidence of slightly elevated AST levels.

Striking elevations in AST levels are observed in the serum of almost all patients with acute hepatic necrosis. In patients with cirrhosis of the liver there is a 60–70% incidence of elevated AST levels. Obviously the early detection of an abnormal rise in AST levels can lead to more rapid and accurate diagnosis of heart and liver disease.

Elevated AST levels have even been correlated with various cancers. Approximately half the patients with metastatic carcinoma have elevated serum AST levels in the same range as patients with cirrhosis and posthepatic jaundice. Less frequently such moderately elevated AST levels are observed in patients with lymphoma and leukeumia. See, Todd-Sanford, *Clinical Diagnosis By Laboratory Methods*, W. B. Saunders Co., 14th Ed., pp. 693–723 (1969).

Elevated levels of AST have also been correlated with active periodontal disease. Periodontal diseases are inflammatory conditions of microbial etiology affecting the supporting tissues of the teeth. Typically, periodontal disease encompasses two major subclasses of disease, gingivitis and periodontitis. Gingivitis is characterized by inflammation of the gums in the absence of bone and attachment loss. Periodontitis is generally accepted to be an advanced stage of gingivitis characterized further by formation of periodontal pockets between the gum tissue and tooth. Severe cases of periodontitis are associated with loss of bone from the tooth and weakening of tooth attachment, eventually leading to tooth loss. The most common form of periodontitis among American adults is chronic inflammatory periodontitis (CIPD) and is characterized by loss of attachment of periodontal ligament to cementum, apical migration of junctional epithelium, and loss of alveolar bone. Both gingivitis and periodontitis are further characterized by accumulation of crevicular fluid (a transudate of serum) at the junction of the teeth and gums.

Presently available methods for identifying periodontal disease are largely subjective involving such criteria as bleeding on gentle probing, pocket depth, attachment loss, and radiographic evidence of bone loss. Unfortunately, these clinical indicators, with the exception of bleeding on probing, are generally acknowledged to reflect past disease and prior damage rather than active disease. Moreover, the diagnostic value of bleeding on probing has even been questioned. See Haffajee, A. D., et al, J. Clin. Perio. 10:257–265 (1983).

Other methods have been proposed for the diagnosis of periodontal disease. Because both gingivitis and periodontitis are characterized by accumulation and flow of crevicular fluid at the gingival sulcus and pockets, measurement of the volume of crevicular fluid present at a site has been proposed as diagnostic for periodontal disease. For example, an instrument, called a Periotron (Harco Electronics Ltd., Winnipeg, Canada), measures the volume of crevicular fluid absorbed by small strips of porous paper (Periopaper) inserted into the crevicular space between the teeth and gum.

Following the above observations of AST levels being correlated with various disease states, a variety of assays for AST have been proposed. The assays typically involve the chemical derivatization of oxaloacetate, a product of the AST-catalyzed reaction of aspartate (Asp) with 2-ketoglutarate:

$$\text{Asp} + \text{2-ketoglutarate} \xrightleftharpoons{\text{AST}} \text{oxaloacetate} + \text{glutamate}$$

Accordingly, EPO Application No. 151,536, proposes such analytical methods as: (i) formation of the highly colored 2,4-dinitrophenylhydrazone (DNP) derivative of oxaloacetate; (ii) formation of the DNP derivative of pyruvate which is produced by the reaction of oxaloacetate with aniline citrate; (iii) conversion of oxaloacetate to malate in the presence of malate dehydrogenase and NADH with the rate of disappearance of NADH followed spectrophotometrically (See also, U.S. Pat. No. 4,059,407 issued to Hochstrasser); and (iv) immunological assay of AST employing anti-AST antibodies which form an AST-antibody complex that can be precipitated from solution.

However, the above methods have several disadvantages. The methods employing DNP typically require long incubation times and the accumulation of oxaloacetate tends to inhibit the forward reaction. The NADH method cannot be followed visually and requires the use of a spectrophotometer. Moreover, NADH is found to interfere significantly with AST activity. Finally, the immunological assay method requires the use of expensive and highly selective AST antibodies.

A method proposed for the detection of AST in sera employs a colorless diazonium salt in a reaction with oxaloacetate to give a colored product. See, for example, U.S. Pat. No. 3,875,014 issued to Forgione. The reaction of oxaloacetate with diazonium salts is generally faster than with DNP. However, the diazonium salt reacts with AST, thereby inactivating the enzyme. Thus, the reaction with substrate must be run before the color development reaction using the diazonium salt. Alternatively, the substrate reagents may be physically separated from the indicator until the AST sample is tested. For example, the method of U.S. Pat. No. 3,875,014 employs two test strips adhered to each other so that an AST-containing sample is exposed to the acid strip where it reacts with L-aspartate and 2-ketoglutarate to give oxaloacetate. The oxaloacetate diffuses along with unreacted AST and substrate to the indicator strip where the reaction with diazo compound takes place. Clearly this method can be expected to only partially avoid the interferences introduced into the assay due to the reaction of AST with the diazo compound.

U.S. Pat. No. 4,801,535 issued to Babler, et al also describes a method for detecting AST employing diazonium salts. This method proposes modifying the reaction conditions of both the acid and indicator solutions so that no visually detectable colored products are observed in the presence of subthreshold levels of AST. However, since the diazonium salt indicator inhibits AST activity it is again necessary to keep the indicator and sample containing AST physically separated until the reaction with substrate is complete. Consequently, the results of the analysis must be subjectively interpreted.

In view of the problems associated with analytical methods employing DNP or diazonium dyes, alternative methods for determining AST are desired. One approach is suggested by the work of Recasens, M., et al, Biochemistry, 19, 4563 (1980) who report that AST is identical to cysteine sulfinate aminotransferase. This observation has suggested the use of L-cysteine sulfinic acid (CSA) as a substrate in place of L-aspartate in assays for AST. When CSA is employed as substrate in the presence of 2-ketoglutarate, AST catalyzes the conversion of CSA to beta-sulfinylpyruvate, which decomposes nonenzymatically to pyruvate and sulfite ion:

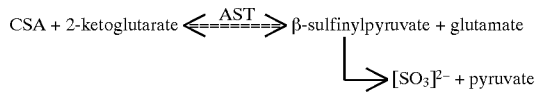

Direct assay techniques have been proposed for the determination of AST using CSA as a substrate. Such techniques involve direct monitoring of substrate or products without interposing any other reactive agent. However, sophisticated instrumentation is required to allow such direct observation of the species involved. Such a method is described in Japan patent 62272998 for the determination of mitochondrial AST.

A simpler method proposed for determining AST using a CSA substrate involves coupling the enzymatic reaction with a non-enzymatic reaction that generates a readily detectable product, e.g., a fluorescent product. One such method proposes reaction of the sulfite ion product species, resulting from the reaction of AST with CSA, with a fluorescent reagent such as (N-9-acrylidinylmaleimide (NAM)). Akasaka, K., et al, Anal.Lett., 18(B3), 357–68 (1985). This method is reported to be highly sensitive but requires high-pressure liquid chromatography as well as a fluorometer to monitor the reaction. See also, Japan patent 60188099.

Another method for determining AST using CSA as substrate proposes use of a colorimetric indicator, nitroblue tetrazolium, in the presence of a coupling agent, phenazine methosulfate. Yagi, T., et al, Anal. Biochem., 110, 146–49 (1981). The phenazine methosulfate serves as an electron transfer mediator to catalyze the reduction of the indicator. After the colored formazan products are formed, acetic acid solution is used to quench the reaction and a dual wavelength thin-layer chromatography scanner is used to quantitate the enzyme activity. Hence, a multiple step process requiring sophisticated equipment is again required. Also, the electron transfer mediators employed are sensitive to light and air.

Clearly a need exists for a simplified and faster method for detecting and quantitatively determining the presence of AST in sera and crevicular fluid. Such method should be compatible with eye-readable assay kits, i.e., should not require use of a spectrophotometer. The method should be free of interferences from contaminants in the examined fluids. Most significantly, the method and associated kits should not require subjective evaluation by the user so that relatively untrained persons can perform needed tests in the home or office under minimal supervision.

BRIEF SUMMARY OF THE INVENTION

The present invention relates to novel methods and kits for performing assays on biological tissues and fluids having elevated levels of aspartate aminotransferase (AST). Elevated AST levels have been shown to be associated with a number of diseases in mammals, such as periodontal disease, heart disease, and cirrhosis of the liver. Thus, the present methods and kits can be employed to identify these diseases in humans. When periodontal disease is desired to be detected, a crevicular fluid sample from the patient is assayed, and when a disease afflicting a body organ is desired to be detected, a bodily fluid sample is assayed.

The instant methods comprise contacting a bodily fluid sample from a mammal with a preselected substrate for AST and a preselected indicator under predetermined reaction conditions. The indicator is selected so that it is substantially nonreactive with both AST and the substrate under the reaction conditions. In the presence of AST at least some of the substrate is converted to a product species that reacts with the indicator to form a signal species. The amount of signal species formed over the course of the reaction is determined, which is related to the amount of AST in the sample.

In a preferred embodiment the preselected substrate is cysteine sulfinic acid (CSA). The action of AST on CSA under the reaction conditions causes evolution of sulfite ion which is subsequently detected.

In a further preferred embodiment, formation of sulfite ion product is visually monitored by its reaction with a colored organic dye. Suitable dyes include derivatives of di- and triarylmethine compounds, such as malachite green, methyl green, guinea green B, ethyl violet, acid fuchsin, basic fuchsin, pararosaniline chloride, pararosaniline acetate, and aurin sodium salt. The results of the AST assay correlate with the presence and severity of disease in the affected tissue.

An instant method may further comprise measuring the initial rate of reaction of indicator with product species when the rate of product formation is related to AST concentration in the fluid sample. Alternatively, the method will comprise allowing the reaction to go to completion then determining whether the indicator response exceeds a predefined threshold value. When the indicator response exceeds such an "endpoint", a positive finding of elevated AST is indicated with a concomitant indication of active disease in the examined tissue.

The instant invention also affords assay kits for identifying AST-related disease, e.g., heart or liver disease, in humans. A kit of the invention comprises a buffered aqueous solution of cysteine sulfinic acid (CSA) as substrate for AST. A kit also comprises an assay plate provided with a plurality of wells each defining a volume sufficient to hold a solid indicator support and a portion of CSA solution adequate to perform at least one assay, i.e., an assay using one indicator support. A kit may also comprise a plurality of solid indicator supports comprising a triarylmethine dye affixed to a solid matrix, with the dye reactive with sulfite ion but substantially nonreactive with both CSA and AST.

A kit may also comprise a means for collecting test fluids from the patient, such as with commercially available Periopaper. The collected fluid will be contacted with the CSA in the presence of the dye. Visible changes in the optical density of the dye correlate with the severity of disease in the patient. Preferred media for delivery of the dye include impregnated polymer films and bibulous materials, such as filter paper.

An instant kit optionally comprises a color contrast agent proximate to or admixed with the dye to enhance the visible contrast of the agent. When the selected dye is a malachite green compound, a suitable color contrast agent is rhodamine B.

Further preferred embodiments of the present assay kits will comprise a wetting agent to assist in quantitatively transferring collected fluid to the test medium. Also, the assay kits will usually comprise a chelating compound, such as ethylenediaminetetraacetate (EDTA) to prevent interferences from metal ions in solution. Still further preferred embodiments of the instant kits will include a ketoglutarate salt admixed with the CSA to serve as an acceptor substrate. Also, the kits may comprise a zinc salt compound admixed with the indicator in order to prolong the useful life of the indicator.

The present inventive methods and kits thereby afford simplified yet sensitive formats for the determination of AST. The assay may be formatted conveniently as a test strip or indicator film. The methods can be performed rapidly by relatively untrained persons using portable eye-readable test kits as well as standard colorimetry or reflectometry devices. Also, because the instant methods and kits afford analyses for AST that are more objective than previously proposed techniques, the likelihood of false negative or false positive indications is significantly reduced.

The presently described novel methods and kits will be more fully understood upon review of the following discussion, which includes specific examples of the invention, and the appended claims.

DETAILED DESCRIPTION OF THE INVENTION

A present inventive method involves determining the AST level of a bodily fluid sample from a mammal. The fluid sample may be crevicular fluid, sera, or fluid withdrawn from a particular organ, e.g., cerebrospinal fluid. The bodily fluid sample is contacted with a preselected substrate for AST and a preselected indicator under predetermined reaction conditions. The indicator is selected so that it is substantially nonreactive with both AST and the substrate under the chosen reaction conditions. An indicator is "substantially nonreactive" with another component of the instant invention when the detected physical property, e.g., color, of the indicator is substantially unchanged in the presence of the component under the reaction conditions of the assay. However, in the presence of AST at least some of the substrate is converted to a product species that is reactive with the indicator. A response to product species by the indicator is observed over the course of the reaction and the degree of indication so determined can be correlated with a predetermined stage of disease.

The enzyme aspartate aminotransferase [AST; EC 2.6.1.1; L-aspartate:2-oxoglutarate aminotransferase] (also known as glutamic aspartic transaminase, glutamic aspartic aminotransferase, glutamic aspartic aminopherase, glutamic oxalacetic transaminase, GOT, G.O.T., or GO-T) (hereinafter referred to as AST) catalyzes the reaction of L-aspartate with 2-ketoglutarate to give oxaloacetate and glutamate. Pyridoxal phosphate is required as a prosthetic group.

AST is found in both the mitochondria and cytosol of eukaryotic cells. The mitochondrial and extra-mitochondrial forms of AST differ in their physical and chemical characteristics and amino acid composition, i.e., they are isozymes. Both forms have a molecular weight of about 90,000 daltons and consist of two approximately equally sized subunits. The fractional determination of cytosolic and mitochondrial AST is useful for the clinical diagnosis of hepatitis, myocardial infarction, etc. Release of AST into the bloodstream at elevated levels is believed to occur upon the death of cells due to the disease condition.

AST is involved in a variety of catabolic and anabolic pathways for amino acids. See, e.g., Lehninger, A. L., *Biochemistry*, 2nd ed. (Worth Publishers, New York, 1975). AST is found in detectable levels in plasma, bile, cerebrospinal fluid, saliva, and gum. See, e.g., J. King, *Practical Clinical Enzymology* (D. Van Nostrand Co. Ltd., Toronto, (1965), pp. 122. Increased levels of blood serum AST have been correlated with acute myocardial infarction, pulmonary embolism, acute pancreatitis, viral and toxic hepatitis, active cirrhosis, obstructive jaundice, muscular dystrophy, acute dermatomyositis, polymyositis, paroxysmal myoglobinuria, and other diseases in various body organs. Increased levels of AST in cerebrospinal fluid have been reported in glioblastoma, stroke and idiopathic epilepsy seizures. See King, supra, pp. 135–136. However, the fact that elevated levels of AST in crevicular fluid correlate with active periodontal disease has only recently been discovered.

The level of AST present in an examined serum sample is "elevated" when the amount of AST is substantially in excess of the level of AST normally found in the blood serum of healthy adults of the species being tested. The normal human adult range of serum AST is typically about 6–40 International Units (I.U.), depending on temperature, when assayed by the procedures described below. See King, supra, p. 134. One I.U. is defined as the amount of AST that will convert 1 nanomole of substrate per minute.

A. Assay Methods

A sample of bodily fluid to be examined for AST level may be obtained from any external or internal tissues producing bodily fluids. Suitable samples are obtained from bile, blood sera, saliva, cerebrospinal fluid, etc. Methods used to obtain such samples are well-known to those skilled in the art.

Oral fluid samples will be obtained from saliva or crevicular fluid. Samples of saliva may be collected from the mouth by a variety of means such as adsorption onto porous solid support materials such as filter paper. Crevicular fluid may be collected from the interface of the gum and tooth by a variety of means including by a microsyringe having a fine (preferably blunt) needle or a capillary tube (preferably calibrated). Samples may also be obtained by means of pledgets, cotton swabs or filamentous material such as dental floss. Preferably, such fluid is sampled by means of absorbent strips of paper or fabric and most preferably by endodontic paper points, e.g., such as Periopaper (Harco Chemical Co.; Tustin, Calif.). The sample is collected by direct contact of the sampling means with crevicular fluid at the interface of the tooth and gum. The volume of sample collected is determined by calibration of the collection means, or alternatively by subsequent measurement. Minor variations in volumes of fluids absorbed (e.g., 10% variations) are not expected to materially alter the accuracy of the testing method. Of course, results obtained for samples of crevicular fluid will more closely reflect the condition of the gum at the position specifically tested than will results obtained for samples of saliva which tend to reflect an average condition of gum in the multitooth area from which the sample is obtained.

According to the present invention suitable AST substrate materials include those substances that are readily converted by AST to products detectable with the preselected indicator material. Preferred substrates include compounds having a sulfinic acid group located "beta" to an amino group, 2-ketoglutarate, and salts thereof. Most preferably, the preselected substrate materials will include cysteine sulfinic acid (CSA) as a "donor" substrate. The reaction of AST with CSA in the presence of an "acceptor" substrate, such as 2-ketoglutarate, results in formation of β-sulfinylpyruvate which decomposes non-enzymatically evolving sulfite ion.

Substrate solutions used in the present invention typically will further comprise one or more pH buffer materials such as phosphates, borates and barbitols. Preferably TRIS-HCl at a pH of 6.0 to 9.0 will be employed. Also, stabilizers such as zinc chloride may be included with the composition. A preferred substrate solution comprises 10–200 mM cysteine sulfinic acid (CSA), 0.5–10 mM 2-ketoglutarate in a 200 mM TRIS-HCl buffer solution having a pH of approximately 8.0. Additional components of the substrate solution may include a metal chelating agent, such as ethylenediaminetetraacetate (EDTA) and a salt component, such as NaCl, as well as a surface active agent, such as Triton X-100.

The substrate solution typically is prepared by initially preparing the buffer medium containing the salt component, the sequestering agent, the buffer components and the surface active agent. In a preferred embodiment, CSA and 2-ketoglutarate are added to the solution followed immediately by adjustment of the pH to a predetermined point. The buffer selected for the assay will be appropriate for buffering in the 4–11 pH range. The pH value selected can be variable due to the isoenzymes of AST having different reaction rates at different pH values and incubation temperatures. The preferred pH range for assay of total enzyme activity will be from about 6.0 to about 9.0.

Exemplary buffers are phosphates, phthalates, "tris" buffers, glycine, citrate phosphate buffer, imidazole buffer, and the like. The preferred buffer system is a "tris" buffer present at about 50 to about 500 millimolar (mM) concentrations.

A sequestering agent is also preferably employed. A suitable agent will be selected from those agents commonly known in the art to chelate multivalent metal ions preferentially over monovalent ions. For example, such agents may be polymers and copolymers containing sulfonic acid moieties, or salts thereof, as exemplified by polyvinylsulfonic acid sodium salt, polyacrylamido-methylpropane sulfonic acid, and polystyrene sulfonic acid, polymers and copolymers containing carboxylic acids and salts thereof, and low molecular weight materials having similar moieties. Most preferred chelating agents include the disodium salt of ethylenediaminetetraacetate (EDTA) and related compounds, present at about 1 to 100 mM concentrations.

Examples of suitable salt components that serve to prevent enzyme adsorption to surfaces are the chlorides of alkali metals, such as sodium chloride, potassium chloride, and cesium chloride. The preferred salt for this purpose is sodium chloride in concentrations from about 50 mM to about 500 mM.

A surface active (wetting) agent may be employed to reduce the surface tension of the solution, thereby improving wettability. Suitable surface active agents include those agents known in the art to be non-denaturing to enzymes. Such compounds as polyoxyethylenes, polyglycidols, alkanolamide derivatives of fatty acids, amino acids, and the like, will be preferred. The amounts employed will range from about 0.01 to about 1% by weight. Most preferably, the surface active agent is Triton X-100 present in about 0.06 w/v. (Concentrations denoted by w/v may be used interchangeably herein with wt % since aqueous solutions are involved.)

The donor substrate for the aminotransferase enzyme in this assay method is preferably selected from cysteine sulfinic acid (CSA) and addition salts thereof. The preferred concentration of CSA in the assay system is dependent on the expected quantity of enzyme being assayed, i.e., it depends on the volume and activity of the sample assayed. For example, in the assay of human blood serum, which has a normal range of less than about 40 units, measurement of an abnormal activity, e.g., up to 3000 units, will require sufficient substrate so that the rate-activity relationship to the time interval of the assay will be nearly linear. Thus, the minimum quantity of substrate required will be dependent on the volume of sample assayed. Sample volumes as small as 0.01 microliters may be assayed. The preferred range of the donor substrate concentration for this assay is variable but will typically range from about 1 mM to about 500 mM.

An acceptor substrate for the aminotransferase enzyme in this assay method is any compound that effectively accepts an amino group from the donor substrate under the reaction conditions. The acceptor substrate preferably includes a source of 2-ketoglutaric acid, usually provided as a salt thereof. The concentration of the acceptor substrate used will be dependent on the corresponding amount of donor substrate employed with the acceptor substrate usually provided in lesser amounts than the donor due to the effect of competitive substrate inhibition. The preferred ratio of 2-ketoglutarate relative to CSA will be from about 1:15 to about 1:20.

The preselected indicator employed in the instant invention is chosen so that it reacts with a product formed upon the reaction of AST with substrate. The indicator is also characterized by not reacting substantially with either AST or substrate. Thus, the indicator will not substantially interact with AST in an inhibitory or destructive manner, nor will the indicator interact with substrate for AST in such a manner that the reaction of AST with substrate is significantly altered or impaired.

Suitable indicators for use in the present invention include those substances capable of reacting with at least one of the products of reaction of AST with the selected substrate. When CSA is the substrate, preferred indicators are sulfite-reactive compounds. The sulfite-reactive compound is an indicator that reacts with sulfite to form a signal species that can be subsequently detected. The signal species will usually be a geometric and electronic derivative of the indicator, e.g., a "leuco" species. A preferred aspect of the invention involves use of an indicator that undergoes a visible color change when it reacts with sulfite ion. Alternative embodiments of the invention employ indicators that respond to the presence of sulfite ion by forming a visible precipitate, producing a fluorescent or chemiluminescent signal, causing a change in the pH or ionic strength of the solution, producing an electrical signal by reaction with an electrode, and the like. Methods for detecting these signals are readily apparent to the skilled practitioner.

Suitable calorimetric indicators include di- and triarylmethine compounds, as well as aza, thia, or oxo analogs of the di- and triarylmethine dyes, polyene and polymethine dyes, aza[18]annulenes, nitro and nitroso dyes, azo dyes, carbonyl dyes, and sulfur dyes subject to the same conditions of readily reacting with sulfite ion and not substantially altering the natural activity of AST in the sample.

Particularly preferred indicators include malachite green and its salts, such as malachite green carbinol hydrochloride, malachite green oxalate, and malachite green - zinc double chloride salt, methyl green, and guinea green B. Also, preferred indicators include acid fuchsin, basic fuchsin, pararosaniline chloride, pararosaniline acetate, ethyl violet, aurin, and their corresponding salt forms in from about 0.0001 to about 1% by weight concentration. Most preferably, the indicator selected will be selected from malachite green, methyl green, and guinea green B. The latter compounds have a greenish color that diminishes in optical density as they react with sulfite ion to give a colorless "leuco" species. See, e.g., E. Jungreis in *Chemical Analysis,* vol. 75, Wiley, p. 185. A preferred concentration of the indicator is about 0.001–0.05 w/v.

Additionally, it is found that the stability of triarylmethine dyestuffs employed in the instant assays can be improved by adding certain components to the indicator solution in small quantities. For instance, certain metal salts known to form complexes with the present dyestuffs yield improvements in indicator dye stability. Preferably, the zinc salts are provided in about 0.001 to about 0.5 w/v concentration and, most preferably, in about 0.25 to 0.35 w/v. Certain indicator double salts of zinc, such as malachite green/2 $ZnCl_2$, may also be employed. Preferred stabilizers include chloride, bromide, acetate, and sulfate salts of zinc.

The present assay method may be performed using either a "rate" or "endpoint" method of measurement. For instance, when the rate method is employed, a dilution series of serum or enzyme standard solutions is prepared. A "blank" sample having no enzyme is also prepared. The source of AST standard is not critical and will conveniently be obtained commercially, e.g., from Sigma Chemical Co., St. Louis, Mo. Preferred standards are human or porcine serum AST. An aliquot of a standard solution is added to an aliquot of a substrate/indicator solution contained in a cuvette in a calorimeter. The cuvette is irradiated with light at a wavelength corresponding to the maximum visible absorbance for the indicator used and the absorbance change with time is monitored. The observed change in absorbance (optical density) is related to the AST concentration in each sample. When reflectometric methods are employed to determine the AST level, the observed changes in reflectance will similarly be related to AST concentration.

A plot of absorbance against time for each reaction will have an initial linear region followed by a curved region as the reaction proceeds. A portion of this plot is chosen in which all dilutions of the standard yield well behaved monotonically decreasing absorbance over the region and the rate of each reaction is determined over an appropriate time interval. Preferably, the time interval will be taken as within about ten minutes of contacting the fluid AST-containing sample with substrate and indicator. Since the measured absorbance is proportional to indicator concentration, the rate of decrease in measured absorbance is directly proportional to the rate of decrease in indicator concentration. The measured absorbance will be proportional to AST activity as long as the reaction of AST with substrate is much slower than other reactions, i.e., the AST-substrate reaction is rate-limiting. Under the reaction conditions described herein, the reaction of AST with CSA will be much slower than the decomposition of β-sulfinylpyruvate and the reaction of sulfite ion with indicator.

A standard curve of the observed reaction rates versus enzyme concentration is then prepared from which a regression analysis yields a standard algebraic expression. Typically, the curve obtained will have the reaction rates essentially linear with respect to AST concentration. If the plotted data yield an unsatisfactory nonlinear curve, a linear curve can usually be obtained via another series of dilutions. Typically, the above curve will be linear in the region of 10–125 AST units/L.

A sample having unknown AST concentration may then be analyzed either by application of one standard volume unit or by serial dilutions of the sample leading to a range of activity values related to the particular dilutions of the sample. In the latter method, the ascertained enzyme levels will nest according to the appropriate dilution factors so that AST units may be determined with confidence.

B. Diagnostic Kits

Diagnostic kits employing the present assay method are also contemplated within the invention. The kits are preferably portable and eye-readable, i.e., can be visually monitored by the user without need for any instrumentation. An instant kit comprises an aliquot of a buffered aqueous CSA solution sufficient to perform at least one assay. Also, a kit comprises an assay plate provided with wells therein for containing the instant assay reagents. Additionally, a kit provides a triarylmethine dye that reacts with sulfite ion but is substantially nonreactive with AST under the defined reaction conditions. The triarylmethine dye is preferably affixed to a solid matrix, as by impregnation, to give a solid indicator support. The solid indicator support can be provided separate from the assay plate or proximal the plate, as with an adhesive. Preferably, a plurality of solid indicator supports are fixably attached to the assay plate within the wells thereof.

The collected sample containing AST enzyme is conveniently placed in a microwell device of the kit. The microwell device, e.g., plate, of the kit is made of a suitable material that is chemically inert to the assay reagents. For instance, the plate can be made of a rigid plastic material, e.g., polycarbonate, polyvinylchloride, polypropylene, and the like, substantially free of plasticizing compounds that might interfere with the assay. The plate may be opaque or clear. A preferred embodiment of the invention employs a plate having a white reflective surface.

The microwell device is provided with a plurality of indentations each having an adequate capacity to contain the sample and reagents used in the assay. A portion of substrate solution prepared as described herein is added and the reaction is allowed to proceed at a predefined temperature for a predetermined period of time. The color of the assay reaction is then compared to a standard reaction performed simultaneously or a reference color comparison chart, i.e., an "endpoint" is identified.

Typically, the indicator support comprises an indicator medium affixed to, i.e., contained on or in, a solid matrix. For example, a polymeric film, e.g., polyvinylalcohol, loaded with indicator medium can be used. Alternatively, a bibulous material, e.g., filter paper, impregnated with a sulfite-reactive indicator solution can be employed. The indicator medium may further include triarylmethine dyestuffs, stabilizers, binder resins, color contrast dyes, and the like.

Preferably, the novel eye-readable kits employing this assay method will utilize an indicator solution comprising triarylmethine dyestuff, color contrast dyestuff, stabilizer, a surface active material, and a binder resin prepared in high purity water or an alternative solvent system in which all components are soluble, such as the lower boiling alcohols and mixtures thereof. The prepared solution is then impregnated on a bibulous medium or cast onto a smooth level surface and allowed to dry. The drying process may be accelerated by forced air flow, heating, or a combination allowing removal of the solvents. A substrate-containing layer may be prepared in similar fashion except that it has been found advantageous to employ freeze drying lyophilization in this case.

When a polymeric film is used to support the instant indicator reagents, the solid matrix preferably comprises a binder resin to affix the reagents to the matrix, as by dispersing the reagents therein. The binder resins used in preparing the instant kits are those resins soluble in the same solvent systems as the dyestuffs and other components. They are generally film-forming materials and may be present as mixtures of compatible resins or as mixtures containing the resins and suitable plasticizers to improve the coating properties as known in the art. Examples of suitable binder resins include the various gums such as gum arabic, guaiac, guar, mastic, and xanthan, as well as soluble synthetic resins such as polyvinylalcohol and copolymers thereof containing vinyl acetate, vinyl ether, or similar co-monomers, polyvinylpyrrolidone and copolymers thereof, polyvinylethers and copolymers with carboxylic acid containing comonomers, polyglycols, polyacrylates, polymethacrylates, polyethersulfones, and the like. A preferred binder resin for these kits is polyvinylalcohol (PVA) of various viscosity grades and degrees of hydrolysis present from about 0.1 to about 20% by weight.

Color contrast dyestuffs may optionally be provided in eye-readable kits employing this method. Such color contrast agents are particularly desirable when the assay results in an absence of coloration, e.g., when a triarylmethine dyestuff has been consumed. The color contrast agent is affixed to the solid matrix of the indicator support either through direct loading of the agent onto the matrix or by locating the color contrast agent proximal to the solid matrix. For example, when malachite green is the triarylmethine dyestuff used, a bluish green color resulting from loading the dye into impregnation paper disappears upon consumption by the assay. Through the addition of a secondary visible indicator that does not interfere with and is unaffected by sulfite ion or other reagents in the kit, the color and threshold of color perception of the endpoint may be varied. Preferred secondary color indicators include auramine O, safranine O, and rhodamine B at concentrations of about 0.01 to about 1 w/v. Alternatively, a colored backing may be provided behind the microwell, film, impregnated paper, etc., used in the assay.

The collected fluid sample, substrate, and indicator solution are mixed and incubated under predefined conditions. These conditions are selected so that no significant detection of AST-catalyzed reaction product will be formed in the presence of a subthreshold amount of AST in the fluid sample. The conditions, however, are such that the presence of a suprathreshold quantity of AST will result in formation of a sufficient quantity of enzyme-catalyzed reaction product to effect a detectable change in a preselected indicator. A suitable threshold value for the assay will depend on the disease state tested for and the types of sample analyzed. The quantity of AST present affects the rate of reaction with substrate and therefore the rate of reaction of indicator. Since the forward reaction of substrate may be inhibited by the presence of competing substrates, care must be taken to preclude the presence of undesired competing substrates which are known to significantly inhibit AST activity. The present methods have been shown to be effective at detecting AST levels as low as 800 microunits. Consequently, dilution to obtain desired threshold values for test solutions may be appropriate.

Optimal reaction conditions will depend on the specific application of the instant method and are easily determined for particular substrates and indicators according to well known techniques in the art. However, the pH of the reaction will typically be in the region 6.0–9.0. The temperature of reaction will usually be in the range of about 20°–35° C. Also, the time required for analysis will typically be less than about one hour.

The reaction solutions employed in the instant kits typically are packaged and stored under biologically sterile conditions. Accordingly, the solutions will usually be stored in containers under an inert gas atmosphere.

An instant assay kit may also comprise a suitable enzyme poison for quenching the assay reagents at some desired point in the assay. For example, an acidic solution capable of halting the activity of AST may be provided in a container of the kit. Other quenching agents will be apparent to the skilled practitioner, as will various modes of poison delivery. For instance, the assay plate of an instant kit may be provided with a moveably attached or detachable lid containing the desired poison. The reaction is quenched upon contacting the poison with the assay reagents.

EXAMPLES

The following examples illustrate but do not limit the scope of the present invention.

1. Determination of Standard AST Curve

In this example a standard curve of optical density versus AST activity is determined with a visible spectrophotometer. The assay is performed in a cuvette transparent to visible light.

Preparation of Substrate Solution

An aqueous solution of the substrate is prepared so that it comprises the following components:

Donor substrate: 91 millimolar (mM) L-cysteinesulfinic acid (CSA)
Acceptor substrate: 9.1 mM mono sodium 2-ketoglutarate
Buffer: 157 mM TRIS-HCl (pH 8.0).
Sequestering agent: 4.5 mM EDTA disodium salt
Salt component: 125 mM sodium chloride
Surface active agent: 0.06 w/v Triton X-100

The above components are dissolved in deionized water and mixed vigorously to dissolve them to the indicated concentrations.

Preparation of Indicator Solution

A separate indicating solution is prepared in deionized water so that it comprises the following components:

Triarylmethine indicator dye: 0.014 w/v Malachite Green Oxalate
Surface active agent: 0.06 w/v Triton X-100

The above ingredients are mixed vigorously to dissolve them in the aqueous medium.

Determination of Standard Curve for AST

A solution containing 850 units/liter of porcine AST (heart), as assayed by an ultraviolet kinetic assay at 340 nm (NAD, Sigma #258-UV), is diluted in 100 mM TRIS buffer (pH=7) containing 0.5% bovine serum albumin such that a series of dilutions containing 25, 12.5, 6.25, 3.13, 1.56, 0.78, and 0.39 units/liter AST activity is obtained. The dilution series is analyzed in triplicate in a Beckman DU-50 UV-Vis spectrophotometer equipped with a six cell thermostated cuvette array employing the kinetic data software package furnished with the instrument. The measurements were performed at 30° C. relative to a reagent blank containing no enzyme activity. Approximately 900 microliters of the substrate solution prepared above is placed in a cuvette having a capacity of approximately 5 milliliters followed by 100 microliters of the triaryl methine dye indicator solution. Approximately 100 microliters of a sample from the AST enzyme dilution series is added to the cuvette, the cuvette is mixed and the assay is started immediately by reading the difference in the reagent blank and the assay cuvette at 614 nanometers absorbance every 15 seconds for 5 minutes total duration. This process is repeated for each AST enzyme sample in the dilution series and the rate of decrease in optical density at 614 nm is determined for each sample in the same time interval. The standardization procedure gave the results presented in Table 1.

TABLE 1

| AST (U/L) | RATE (ΔOD/min) |
|---|---|
| 25.0 | −0.180 |
| 12.5 | −0.112 |
| 6.25 | −0.077 |
| 3.13 | −0.056 |
| 1.56 | −0.046 |
| 0.78 | −0.042 |
| 0.39 | −0.039 |

A regression analysis performed on the above data gives the following equation with a correlation coefficient of 0.999:

Rate=0.00574 (AST)+0.038189

2. Determination of Human Serum AST

In this example, the applicability of the assay method as described in Example 1 was demonstrated for authentic human serum. The assay was performed as in Example 1 except that the level of L-cysteinesulfinic acid was 100 mM, the level of mono sodium 2-ketoglutarate was 10 mM, the level of TRIS buffer was 175 mM, and the level of disodium EDTA was 5 mM.

A series of dilutions of an authentic human sera control (Accutrol, Sigma) were made employing 100 mM TRIS buffer (pH=7.8) to give the nominal AST activities shown in Table 2. The assay method was performed as described in Example 1.

TABLE 2

| AST (U/L) | RATE (ΔOD/min.) |
|---|---|
| 11.88 | −0.212 |
| 5.94 | −0.115 |
| 2.97 | −0.057 |
| 1.48 | −0.028 |
| 0.74 | −0.012 |

A regression analysis on the above data gave the following equation with a correlation coefficient of 0.9987:

Rate=0.01791 (AST)+0.00237

3. Preparation and Use of Indicator Film Assay Kit

In this example, an assay kit for the enzyme AST is formatted to emulate the measurement of enzyme activity in crevicular fluid samples collected from oral sites having elevated AST enzyme activity due to the presence of periodontal disease. The clinical cutoff level for disease indication has been determined to correspond to less than 800 microunits/liter activity in the sample. The substrate solution was prepared as in Example 1 except that the level of L-cysteinesulfinic acid was 100 mM, the level of mono sodium 2-ketoglutarate was 10 mM, the level of the TRIS buffer was 200 mM, and the level of EDTA disodium salt was 5 mM.

Preparation of Triaryl Methine Dye Indicator Films

A solution containing 8% polyvinyl alcohol (Air Products V-165) is prepared by boiling 1 liter of deionized water containing 0.06% Triton X-100 and slowly adding 80 grams of the polymer with good mixing. While still hot the solution is divided into two 500 ml portions in bottles with tightly sealing caps. Into the first bottle is added 175 milligrams of malachite green oxalate, 100 milligrams of rhodamine B chloride, and 1.0 grams of zinc chloride. Into the second bottle is added 175 milligrams malachite green oxalate, 250 milligrams auramine O monohydrochloride, and 1.0 grams of zinc chloride. The two bottles containing the ingredients are placed on a rolling mill and thoroughly mixed until homogenous. They are then removed from the mill and allowed to stand until all entrained air bubbles have diffused from solution. After cooling to room temperature, a 70 ml aliquot of each solution is removed and poured evenly over 8"×14" inch glass plates. The plates were placed on a leveled table in a hood and allowed to evaporate to dryness overnight. This procedure resulted in films with thickness ranging from 1.7 to 2.0 mils. The dried films were then punched into circles having a diameter of 0.25 inches.

Preparation of Assay Kits

Sheets of opaque high density polyethylene stock having a thickness of 0.125 inches were cut into 3"×4" rectangles. Two rows of six holes having 0.5 inch centers and diameters of 0.25 inches were drilled into the rectangles in a symmetric manner. Strips of 10 mil thick acetal plastic were laminated with a non-acrylic 2 mil transfer adhesive and cut into 3"×4" rectangles. The release liner was removed from these and the acetal parts were laminated to the high density polyethylene parts. This process resulted in a watertight construction having adhesive in the bottom of the resulting wells. Into each of these wells was placed a circle of the indicator film prepared above such that one row of six wells contained blue circles (malachite green oxalate and rhodamine B chloride) and one row contained green circles (malachite green oxalate and auramine O mono HCl).

Evaluation of the Assay Kits

A series of standardized enzyme solutions containing 400, 600, 800, 1000, 1200 microunits/microliter AST concentrations were freshly prepared. One microliter of each sample was placed in a well containing color indicator circle in such a manner that the two rows had ascending concentrations of enzyme AST activity and one blank solution in each row. A countdown timer was set for ten minutes and started. Into each of the wells was placed 25 microliters of the substrate solution. After ten minutes the assay was scored visually. For AST enzyme levels of 800 microunits and above, the color of the blue indicator circles was pink and the color of the green circles was yellow. For AST enzyme levels ranging from zero to 600 microunits only a gradation of color to lighter shades of blue or green resulted. In both the blue and green indicator assays a clear and distinct calorimetric endpoint threshold was exceeded at the 800 level and above.

4. Determination of Abnormal Serum AST Levels

In this example, the colorimetric endpoint assay kit format of Example 3 was evaluated for distinguishing normal verses abnormal serum based controls. An assay kit and a substrate solution were prepared as in Example 3. Freshly obtained normal and abnormal Accutrol chemistry standards (Sigma) known to contain 20–25 units/L AST activity in a human serum base for the normal control and 100–120 units/L for the abnormal control were employed. Into two wells of each row of the assay kit were placed zero AST, 10 microliters of the normal control, and 10 microliters of abnormal control. A countdown timer was set for 5 minutes and started. Into each of the wells was placed 25 microliters of the substrate solution prepared as described in Example 3. After 5 minutes elapsed time the assay kit was scored visually. The blank cells did not change color, the normal controls were a lighter shade of either blue or green, and the abnormal controls were distinctly beyond the calorimetric endpoint threshold. In the case of the blue indicator circle the abnormal control endpoint color was a bright red and in the case of the green indicator circle the endpoint color was a deep yellow.

5. Impregnated Bibulous Media Kit

In this example, the use of impregnated bibulous media is illustrated for the triarylmethine dye indicator component of an assay kit.

Preparation of Triaryl Methine Dye Indicator Paper

A solution containing 1% polyvinyl alcohol and 0.06% Triton X-100 is prepared in deionized water as in Example 3. To 500 ml of this polymer solution is added 150 milligrams of malachite green carbinol hydrochloride, 150 milligrams of rhodamine B chloride, and 55 milligrams zinc chloride. The mixture is stirred until all components have dissolved. An aliquot of this mixture is placed into a beaker and 1 inch wide strips of Schleicher and Schuell impregnation paper 2043-A having a basis weight of 83 grams/square meter and a water absorbency of 1.3 grams/100 square centimeters are dipped into the solution for 1 minute. The papers are removed and drained for 30 seconds then laid on a stainless steel tray and dried in a convection oven for 30 minutes at 65° C. After removal from the oven the impregnated strips are punched into 0.25 inch diameter circles.

Assay of AST

A substrate solution is prepared as in Example 1 except that the level of L-cysteinesulfinic acid is 10 mM, mono sodium 2-ketoglutarate is 1.0 mM, TRIS-buffer is 200 mM., and disodium EDTA is 5.0 mM. An assay placket is fabricated from precut, drilled, and laminated components as in Example 3. Into one row of wells is placed the punched impregnated circles and 1 microliter of prestandarized AST enzyme solutions containing 0, 200, 400, 600, 800, and 1000 microunits/microliter enzyme activity. A countdown timer set for 10 minutes is started and 25 microliters of substrate solution is added to each well. At the end of ten minutes the assay is visually scored. The well containing the blank was unchanged in color. The wells containing less than 800 microunits have a lighter blue color ranging almost to purple at the 600 level. The wells containing 800 and higher levels are distinctly pink in color indicating the threshold level of the colorimetric indicator has been exceeded.

6. Evaluation of Alternative Indicators

Other dyestuffs were evaluated for application to the assay of the enzyme AST after they were found to undergo a color change in the presence of sulfite ion in aqueous solution. The evaluations were performed by making a 0.03% solution of the respective dyestuff in 1% polyvinyl solution containing 0.06% Triton X-100 and impregnating the 2043-A paper as in Example 5. After drying, the impregnated papers were punched into 0.25 inch circles and placed in pairs in an assay device as fabricated in Example 3. A substrate solution was prepared as in Example 5 except that the level of L-cysteinesulfinic acid was 20 mM and the level of mono sodium 2-ketoglutarate was 2.0 mM. A standard solution of AST having an activity of 1500 microunits/microliter was prepared. The respective dyestuffs were evaluated by running a blank reaction side by side with a reaction having 1.0 microliters of the enzyme solution. Approximately 25 microliters of the substrate were added to each well and the reactions were evaluated after 10 minutes. Dyestuffs that did not exhibit a visible color change progressive with time relative to the blank reaction were classified as unsuitable for this assay method.

The following dyestuffs exhibited a visible color change progressive with time relative to the blank reaction and were shown to be suitable for practice of the assay method: Methyl Green, Guinea Green B, Ethyl Violet, Acid Fuchsin, Basic Fuchsin, Pararosaniline Chloride, Pararosaniline Acetate, Aurin sodium salt.

Although the present invention has been described in some detail by way of illustration and example for purposes of clarity and understanding, it will be obvious that certain modifications may be practiced within the scope of the appended claims.

What is claimed is:

1. An assay kit for identifying periodontal disease in a patient, said disease correlated to elevated levels of aspartate aminotransferase (AST) in a crevicular fluid sample from the patient, which kit comprises an enclosure containing:
   an aliquot of a buffered aqueous solution of cysteine sulfinic acid (CSA) provided in a container for said aliquot;
   a plurality of solid indicator supports each comprising a triarylmethine dye affixed to a solid matrix, said dye reactive with sulfite ion and nonreactive with both CSA and AST; and
   an assay plate provided with a plurality of wells, each well defining a volume sufficient to hold one of said solid indicator supports and a portion of the CSA solution adequate to perform at least one assay.

2. The kit as in claim 1, wherein the CSA solution further comprises a wetting agent selected from the group consisting of polyoxyethylenes, polyglycidol, alkanolamide derivatives of fatty acids, and amino acids.

3. The kit as in claim 1, wherein the CSA solution further comprises 2-ketoglutarate.

4. The kit as in claim 1, wherein the CSA solution further comprises a sequestering agent selected from the group consisting of polyvinylsulfonic acid sodium salt, polyacrylamido-methylpropane sulfonic acid, polystyrene sulfonic acid, polymers and copolymers containing carboxylic acids and salts thereof, and ethylenediminetetraacetate (EDTA).

5. The kit as in claim 1, wherein the dye is selected from the group consisting of malachite green, methyl green, guinea green B, ethyl violet, acid fuchsin, basic fuchsin, pararosaniline chloride, pararosaniline acetate, aurin sodium salt, and addition salts thereof.

6. The kit as in claim 1, wherein the solid matrix comprises a porous paper.

7. The kit as in claim 1, wherein the solid matrix comprises polyvinylalcohol.

8. The kit as in claim 1, wherein a color contrast agent is affixed to said solid matrix.

9. The kit as in claim 1, further comprising a lid proximal the assay plate, said lid comprises an acidic solution.

10. An assay kit for identifying a disease correlated to elevated levels of aspartate aminotransferase (AST) in a bodily fluid sample from a patient, which kit comprises an enclosure containing:

an aliquot of a buffered aqueous solution of cysteine sulfinic acid (CSA) provided in a container for said aliquot; and an assay plate defining a plurality of assay wells, said assay wells containing a triarylmethine dye that is reactive with sulfite ion but nonreactive with CSA and AST, each of said assay wells defining a volume sufficient to hold the fluid sample and a portion of the CSA solution adequate to perform at least one assay.

11. A method for determining the amount of aspartate aminotransferase (AST) in a body fluid sample from a mammal, which method comprises:

contacting, under AST reacton conditions, a body fluid sample from the mammal with cysteine sulfinic acid (CSA) in the presence of a triarylmethine dye nonreactive with both AST and CSA for a period of time sufficient for at least some of said CSA to be converted to sulfite ions that react with said triarylmethine dye to form a signal species; and determining the amount of signal species formed, and thereby the amount of AST in said sample.

12. The method as in claim 11, further comprising measuring the rate of signal species formation.

13. The method as in claim 11, further comprising determining the endpoint of the reaction of said triarylmethine dye with said sulfite ions.

14. The method as in claim 11, wherein said triarylmethine dye exhibits a visible spectral change during the reaction.

15. The method as in claim 11, where in the AST reaction conditions include a buffered aqueous medium having pH in the range of about 6.0 to about 9.0.

16. A method for detecting an AST-related disease in a patient comprising contacting a fluid sample from the patient with cysteine sulfinic acid (CSA) in the presence of a triarylmethine dye that is nonreactive with both CSA and the fluid sample, and detecting reaction of said triarylmethine dye.

17. The method as in claim 16, wherein the disease is periodontal disease and the sample comprises crevicular fluid.

18. The method as in claim 16, wherein the sample comprises sera.

19. The method as in claim 16, further comprising determining the rate of reaction of said triarylmethine dye.

20. The method as in claim 16, further comprising determining the extent of reaction of said triarylmethine dye.

* * * * *